United States Patent
Eiyama

(10) Patent No.: US 8,807,696 B2
(45) Date of Patent: Aug. 19, 2014

(54) COLORIMETRIC APPARATUS AND COLORIMETRIC METHOD

(71) Applicant: Canon Kabushiki Kaisha, Tokyo (JP)

(72) Inventor: Masato Eiyama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 13/837,173

(22) Filed: Mar. 15, 2013

(65) Prior Publication Data

US 2013/0257971 A1   Oct. 3, 2013

(30) Foreign Application Priority Data

Mar. 27, 2012 (JP) ................................. 2012-072339

(51) Int. Cl.
*B41J 29/393* (2006.01)
*G01N 21/25* (2006.01)

(52) U.S. Cl.
CPC .................................. *G01N 21/251* (2013.01)
USPC ............................................ 347/19; 347/16

(58) Field of Classification Search
USPC ..................... 347/14, 16, 19, 101, 104, 105
See application file for complete search history.

(56) References Cited

U.S. PATENT DOCUMENTS 6,994,432 B2 * 2/2006 Scofield et al. ............... 347/105
8,368,928 B2   2/2013 Kuwahara

FOREIGN PATENT DOCUMENTS

JP   2009-220290 A   10/2009

* cited by examiner

*Primary Examiner* — Juanita D Jackson
(74) *Attorney, Agent, or Firm* — Fitzpatrick, Cella, Harper & Scinto

(57) ABSTRACT

In an apparatus including an irradiation unit capable of irradiating a sheet with at least either visible light or ultraviolet light, and an acquisition unit which acquires a spectral reflectance for each of a plurality of wavelength regions based on light reflected by the sheet, a spectral reflectance acquired by the acquisition unit when the sheet is irradiated with the visible light is stored in a memory unit. A storing unit stores, in the memory unit, a spectral reflectance in a wavelength region shorter than a predetermined wavelength among spectral reflectances acquired by the acquisition unit when the sheet is irradiated with both the visible light and the ultraviolet light.

9 Claims, 8 Drawing Sheets

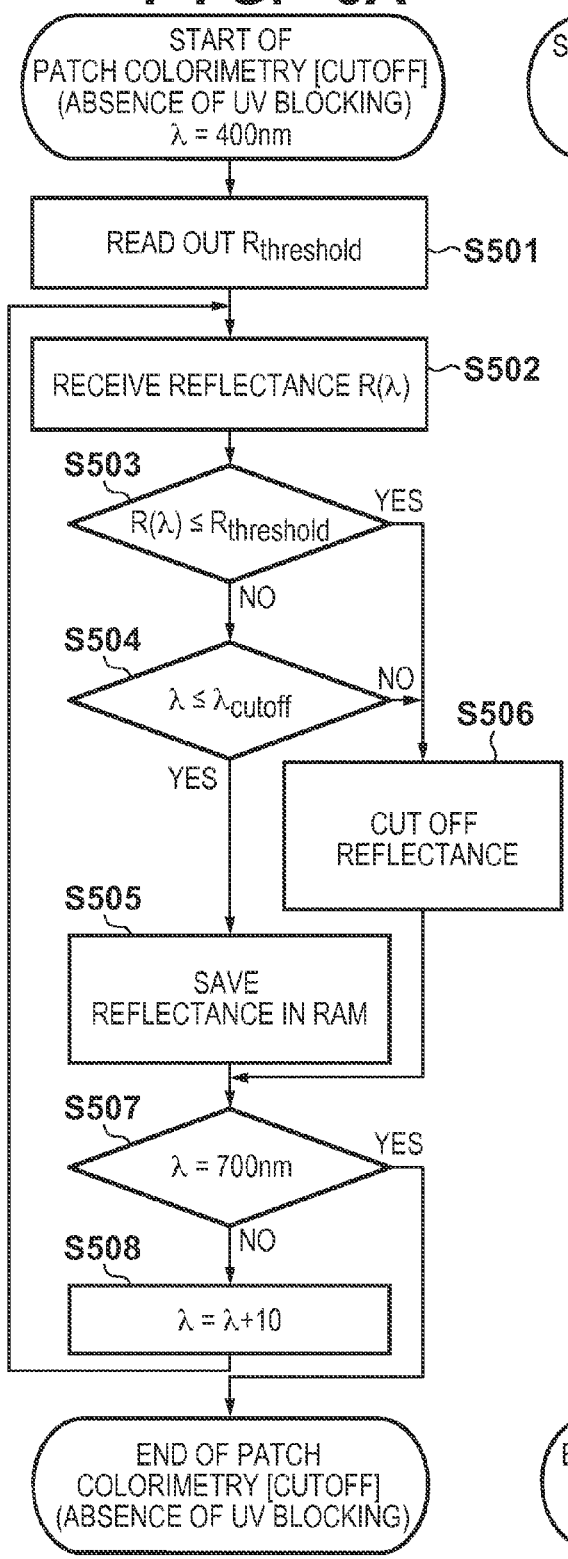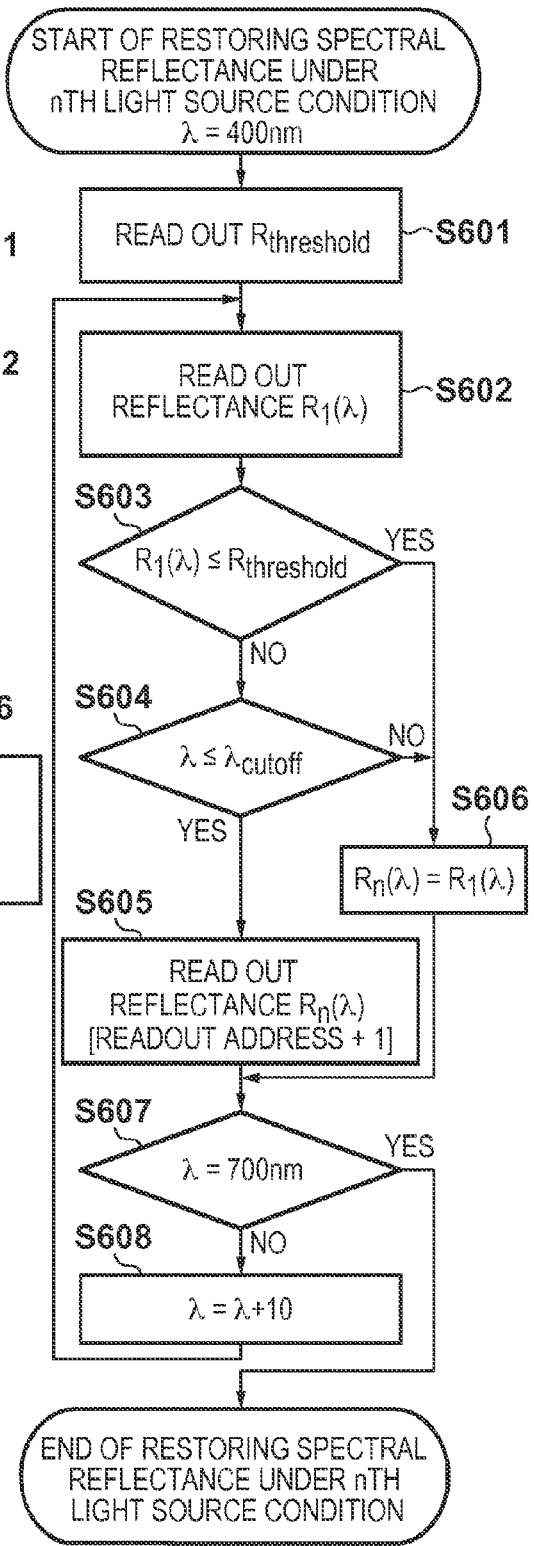

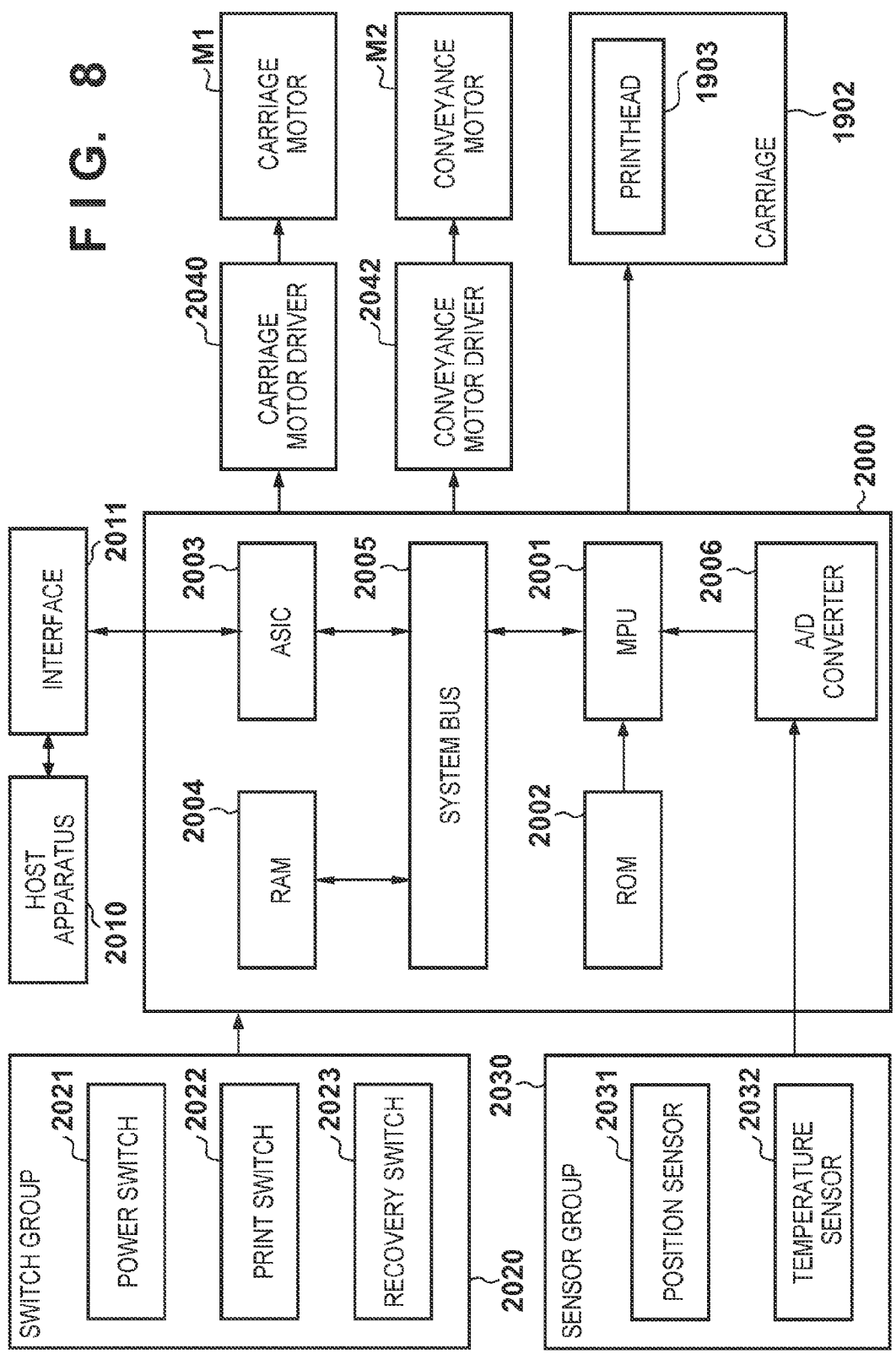

COLORIMETRIC APPARATUS AND COLORIMETRIC METHOD

BACKGROUND OF THE INVENTION

1. Field of the Invention

The present invention relates to a colorimetric apparatus and colorimetric method capable of colorimetry.

2. Description of the Related Art

Recently, due to their high image quality, inkjet printing apparatuses are often used as industrial printing apparatuses for dealing with printed materials. The inkjet printing apparatuses require high reproducibility for even a small color tone difference or slight density unevenness of an output image. The inkjet printing apparatus sometimes includes a plurality of printheads and nozzle arrays for discharging ink of the same color. In this case, the discharge characteristic may differ between the printheads or the nozzle arrays owing to variations of the heat generation amount of a heater for discharging ink or variations of the diameter of a nozzle for discharging ink, failing to obtain a desired color tone in an output image. To cope with such color tone difference, calibration is generally executed. The calibration changes a gamma table used in gamma correction processing for correcting the discharge characteristic of a printhead. For example, a patch image is printed on a sheet using a plurality of printheads and nozzle arrays, and the gamma table is appropriately set again based on the printing result.

The inkjet printing apparatus is often used for proof in printing because the running cost in printing is lower than in another type of printing apparatus. The poof aims at outputting the same result as the tint of a final printed material, so color proof is performed to adjust the color to that of the final printed material, in addition to the above-mentioned calibration. For example, a profile is created so that the same color as a target CMYK or RGB input is output by taking account of the apparatus-specific color reproduction characteristic and the characteristics of a sheet used in color proof. Printing based on the created profile can output the same tint as that of a final printed material.

A colorimeter is used in the above-described calibration and profile creation. It is common to use a reflection spectral colorimeter capable of measuring reflected light in the visible light region for each wavelength band and outputting a chromaticity complying with a colorimetric system such as CIEL*a*b* in accordance with the measurement result. In recent years, inkjet printing apparatuses which include a colorimetric sensor and can perform seamless colorimetry for a printed material are also used.

Recently, there are various types of sheets (printing media) designed for inkjet printing apparatuses, including art paper and Japanese paper. A sheet containing a fluorescent brightener for making output look whiter is sometimes used. When the user selects a sheet from various types of sheets available from third parties and is to print, he needs to create a profile in accordance with an inkjet printing apparatus to be used because the sheet vender does not always provide a profile optimum for all inkjet printing apparatuses.

A fluorescent brightener-containing sheet differs greatly in appearance depending on the intensity of ultraviolet light contained in a light source, even under a light source which looks the same. This is because light in the ultraviolet (UV) wavelength band contained in the light source is excited by the fluorescent brightener contained in the sheet and reflected as visible light. For a light source containing no ultraviolet light region and a sheet containing no fluorescent brightener, an intensity in the wavelength band of the light source becomes equal to one in the wavelength band of light reflected by the sheet. However, when a fluorescent brightener-containing sheet is measured under a ultraviolet light region-containing light source, light in the wavelength band of ultraviolet light is excited by the fluorescent brightener and reflected as visible light. For this reason, an intensity in the wavelength band of ultraviolet light affects the wavelength band of visible light. Even if intensity in the visible light region of the light source remains unchanged, the difference of the spectral intensity in the ultraviolet light region makes the tint look different. This is known as a metamerism phenomenon, in which the tint of an image printed on a sheet looks different depending on the type of observation light source used to evaluate the image. Under these circumstances, in proof and production printing requiring strict color management, light source conditions such as the presence/absence of the ultraviolet (UV) blocking filter of a measurement light source are defined by international standards (for example, ISO13655: 2009, and ISO3664). Recently, the spectral intensity of an ultraviolet light source is also defined to make a measurement light source and environment light source match each other more strictly.

To evaluate an optimal color under an environment light source, a plurality of profiles are created based on the results of measurement under a plurality of measurement light sources. Measurement of the spectral reflectance considers various light source conditions, so the colorimeter is often configured to allow the user to arbitrarily attach or detach an UV blocking filter. Some colorimeters can measure a color under desired conditions by using an ultraviolet light source and visible light source as a plurality of physical light sources and switching between these light sources. Such a colorimeter can be used to easily obtain colorimetric values under a plurality of light sources in profile creation.

In general, the number of patches to undergo colorimetry in calibration is about 300, and the number of patches to undergo colorimetry in profile creation is as many as 1,000. Further, every time one measurement condition is added, the amount of colorimetric result data is doubled. That is, every time the measurement light source is switched, a buffer area for saving a measured spectral reflectance needs to be ensured for the number of patches mentioned above. Generally, the frequency at which colorimetry under a plurality of light source conditions is performed is much lower than the frequency at which colorimetry under a fixed light source condition (for example, closed-loop calibration) is performed. Owing to low-frequency measurement, a large buffer area needs to be ensured. Japanese Patent Laid-Open No. 2009-220290 discloses an arrangement in which a colorimeter is directly controlled by a printer via a USB connection. However, as the number of patches increases, colorimetric result data consumes the limited storage area of the USB.

SUMMARY OF THE INVENTION

An aspect of the present invention is to eliminate the above-mentioned problems with the conventional technology. The present invention provides a colorimetric apparatus and colorimetric method for suppressing an increase in the storage amount of measurement results in colorimetry using a plurality of light sources.

The present invention in its first aspect provides a colorimetric apparatus comprising: an irradiation unit configured to be able to irradiate a sheet with at least one of visible light and ultraviolet light; an acquisition unit configured to acquire a spectral reflectance for each of a plurality of wavelength regions based on light reflected by the sheet; a memory unit;

and a storing unit configured to store, in the memory unit, a spectral reflectance acquired by the acquisition unit in a case where the sheet is irradiated with the visible light, wherein the storing unit stores, in the memory unit, a spectral reflectance in a wavelength region shorter than a predetermined wavelength among spectral reflectances acquired by the acquisition unit in a case where the sheet is irradiated with both the visible light and the ultraviolet light.

The present invention in its second aspect provides a colorimetric apparatus comprising: an irradiation unit configured to be able to irradiate a sheet with at least one of visible light and ultraviolet light; an acquisition unit configured to acquire a spectral reflectance for each of a plurality of wavelength regions based on light reflected by the sheet; a memory unit; and a storing unit configured to store, in the memory unit, a spectral reflectance acquired by the acquisition unit in a case where the sheet is irradiated with both the visible light and the ultraviolet light, and store, in the memory unit, a spectral reflectance in a wavelength region shorter than a predetermined wavelength among spectral reflectances acquired by the acquisition unit in a case where the sheet is irradiated with the visible light.

The present invention in its third aspect provides a colorimetric method comprising: a first acquisition step of acquiring a spectral reflectance for each of a plurality of predetermined wavelength regions based on light reflected by a sheet in a case where the sheet is irradiated with visible light; a first storing step of storing, in a memory unit, a spectral reflectance acquired in the first acquisition step; a second acquisition step of acquiring a spectral reflectance for each of the plurality of wavelength regions based on light reflected by the sheet in a case where the sheet is irradiated with both visible light and ultraviolet light; and a second storing step of storing, in the memory unit, a spectral reflectance in a wavelength region shorter than a predetermined wavelength among spectral reflectances acquired in the second acquisition step.

The present invention in its fourth aspect provides a colorimetric method comprising: a first acquisition step of acquiring a spectral reflectance for each of a plurality of predetermined wavelength regions based on light reflected by a sheet in a case where the sheet is irradiated with both visible light and ultraviolet light; a first storing step of storing, in a memory unit, a spectral reflectance acquired in the first acquisition step; a second acquisition step of acquiring a spectral reflectance for each of the plurality of wavelength regions based on light reflected by the sheet in a case where the sheet is irradiated with visible light; and a second storing step of storing, in the memory unit, a spectral reflectance in a wavelength region shorter than a predetermined wavelength among spectral reflectances acquired in the second acquisition step.

The present invention can suppress an increase in the storage amount of measurement results in colorimetry using a plurality of light sources.

Further features of the present invention will become apparent from the following description of exemplary embodiments with reference to the attached drawings.

BRIEF DESCRIPTION OF THE DRAWINGS

FIGS. 5A and 5B are flowcharts showing the sequence of processing in step S306 in the third embodiment;

FIG. 8 is a block diagram showing the control arrangement of the inkjet printing apparatus.

DESCRIPTION OF THE EMBODIMENTS

Figure 1:
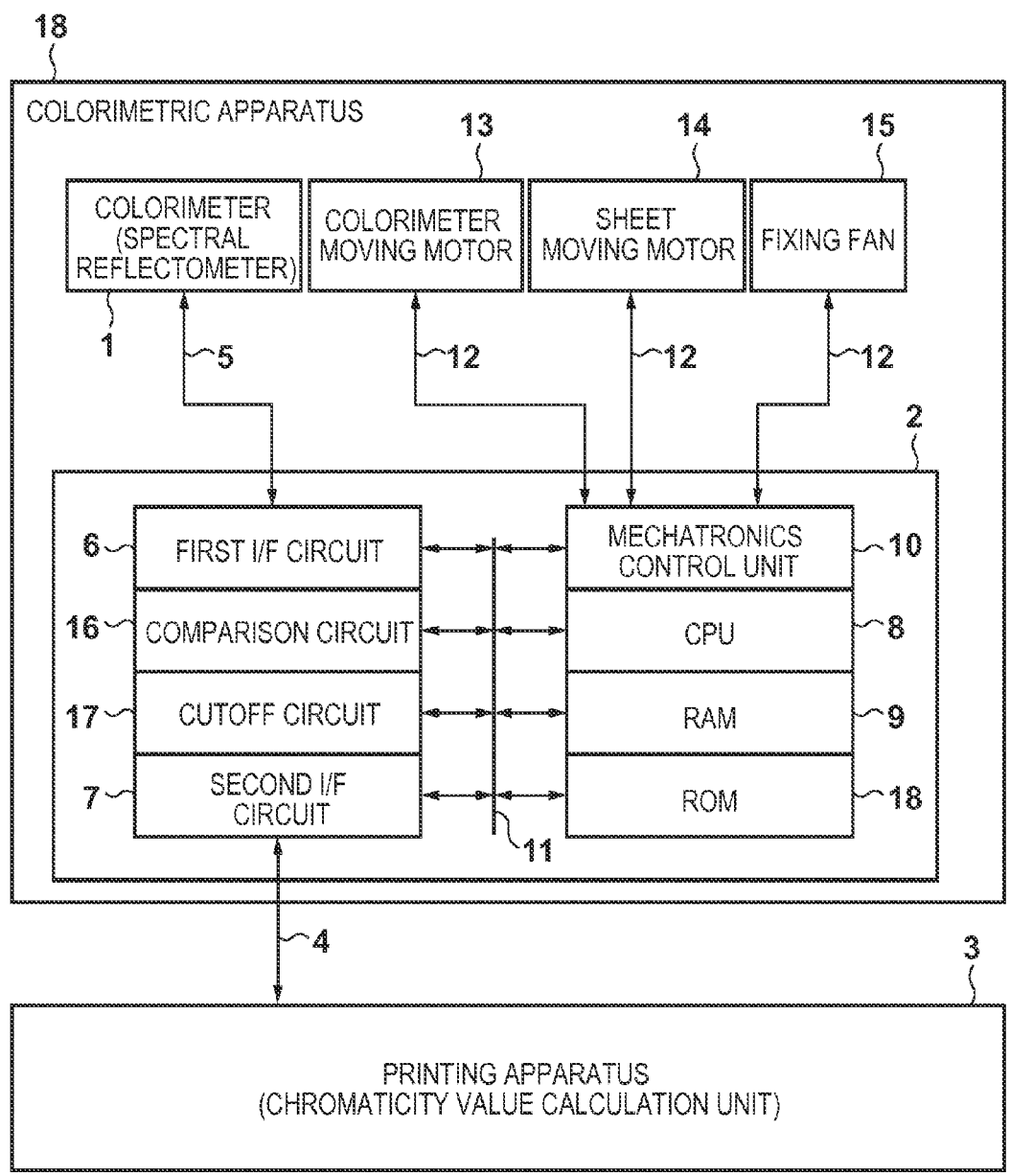
FIG. 1 is a block diagram showing the arrangement of a colorimetric apparatus connected to a printing apparatus.

Preferred embodiments of the present invention will now be described hereinafter in detail, with reference to the accompanying drawings. It is to be understood that the following embodiments are not intended to limit the claims of the present invention, and that not all of the combinations of the aspects that are described according to the following embodiments are necessarily required with respect to the means to solve the problems according to the present invention. Note that the same reference numerals denote the same parts, and a repetitive description thereof will be omitted.

First Embodiment

The first embodiment uses a printing apparatus which prints an image on a sheet serving as a printing medium based on image data. In the embodiment, a measurement apparatus which measures the color of the patch image (to be referred to as a patch hereinafter) of a patch chart, and the printing apparatus may be separated or integrated. The printing apparatus suffices to print an image on a sheet, and, for example, an inkjet printing apparatus is used. The arrangement of the inkjet printing apparatus as an example of the printing apparatus will be described later.

FIG. 1 is a block diagram showing the arrangement of the colorimetric (color measuring) apparatus connected to the printing apparatus. A printing apparatus 3 is, for example, an inkjet printing apparatus, and is connected to a colorimetric control device 2 in a colorimetric apparatus 18. The colorimetric control device 2 includes a first interface circuit 6 and second interface circuit 7 for external connection. A comparison circuit 16 shown in FIG. 1 will be described in the second embodiment. The first interface circuit 6 is connected to a colorimeter 1 via a signal line 5. The first interface circuit 6 transmits an instruction such as white color proof or colorimetry execution to the colorimeter 1, and receives a colorimetric result and information such as an error or status from the colorimeter 1 in response to the instruction. The second interface circuit 7 is connected to the printing apparatus 3 via a signal line 4. The colorimetric control device 2 operates as a host for the printing apparatus 3. The printing apparatus 3 transmits operation instructions necessary for colorimetry via the signal line 4, and receives output data from the colorimeter 1 via the colorimetric control device 2.

The operation instructions necessary for colorimetry include an instruction to move the colorimeter 1 to a position where colorimetry for a target patch is possible, and an instruction about the operation of a fixing fan for fixing a printed patch. A CPU 8 of the colorimetric control device 2 receives an instruction from the printing apparatus 3 via an internal common bus 11, analyzes it, and controls the colorimeter 1, a colorimeter moving motor 13, a sheet moving motor 14, and a fixing fan 15 in accordance with the instruction contents.

The colorimeter 1 is a spectral reflectance measurement device formed from a measurement system for 0° to 45°. The colorimeter 1 has a scan colorimetric function of continuously measuring the colors of patches while moving on a strip of patches at a predetermined speed, and a single colorimetric function of measuring one patch at a fixed position. The colorimeter 1 includes two independent light sources for measurement, that is, an ultraviolet light source (UV-LED) having an emission intensity peak near 360 to 390 nm, and a visible light source (white LED) which emits light in a wavelength band near 400 to 700 nm. The colorimeter 1 splits light reflected on an object to be measured into 10-nm bands in the visible light band of 400 to 700 nm, and outputs spectral reflectance measurement values for 31 wavelength regions after white poof using a reference white plate.

The colorimeter 1 executes a colorimetric operation in accordance with an instruction set received from the colorimetric control device 2. The instruction set received by the colorimeter 1 from the colorimetric control device 2 includes a status output instruction, white color proof execution instruction, and colorimetry execution instruction for the colorimeter 1. As arguments for the colorimetry execution instruction, colorimetric light source conditions are set. The colorimetric light source conditions are, for example, setting of the type of light source such as an A light source, printing evaluation light source D50, reference daylight light source D65, or evaluation fluorescent light source F12, and setting of the presence/absence of UV blocking. Upon receiving a colorimetry execution instruction from the colorimetric control device 2, the colorimeter 1 sets the intensities of the mounted ultraviolet light source and visible light source in accordance with the settings of the colorimetric light source conditions serving as arguments. The colorimeter 1 stores in advance the intensities of the respective light sources such as the intensities of the ultraviolet light source and visible light source for the light source D50.

Next, a colorimetric operation in the embodiment will be explained. First, a patch chart (not shown) which has been printed on a sheet by the printing apparatus 3 and is to undergo colorimetry is output from the printing apparatus 3 and fed to the colorimetric apparatus 18. A plurality of patches are arranged in strips on the patch chart. After feeding, the printing apparatus 3 transmits a fixing instruction to the colorimetric control device 2 by using a predetermined fixing time and rotational speed as arguments in accordance with the sheet type. Upon receiving the fixing instruction, the colorimetric control device 2 controls the sheet moving motor 14 to move the patch chart to a fixing unit (not shown). At this time, the CPU 8 controls the sheet moving motor 14 via a mechatronics control unit 10. After the sheet reaches the fixing unit, the CPU 8 controls the fixing fan 15 via the mechatronics control unit 10 to rotate at a desired rotational speed for a desired time. Upon completion of fixing, the colorimetric control device 2 transmits a normal end status to the printing apparatus 3. Upon receiving the normal end status, the printing apparatus 3 transmits a colorimetry instruction for the patch chart to the colorimetric control device 2.

Upon receiving the colorimetry instruction, the colorimetric control device 2 controls the sheet moving motor 14 via the mechatronics control unit 10 to move the sheet to a colorimetric position. After moving the sheet to the colorimetric position, the colorimetric control device 2 uses a colorimetric light source condition and measurement patch count given by the printing apparatus 3 as arguments for the colorimeter 1, and transmits a colorimetry preparation instruction to the colorimeter 1. Upon receiving the colorimetry preparation instruction, the colorimeter 1 acquires the intensities of the ultraviolet light source and visible light source associated with light sources set in the colorimetric light source condition, and starts preliminary emission of the respective light sources. The preliminary emission is an operation for stabilizing a change of the emission amount immediately after lighting of the LED to a steady state. The preliminary emission time is set in advance for each of the ultraviolet light source and visible light source. After the end of preliminary emission, the colorimeter 1 transmits a preliminary emission end status to the colorimetric control device 2. Upon receiving the preliminary emission end status, the colorimetric control device 2 drives the colorimeter moving motor 13. When the colorimeter 1 reaches the first measurement target patch on a strip, the colorimetric control device 2 transmits a colorimetry start instruction to the colorimeter 1. Upon receiving the colorimetry start instruction, the colorimeter 1 starts colorimetry by the measurement patch count.

The colorimeter 1 transmits the spectral reflectances of all the measured patches to the colorimetric control device 2 via the signal line 5. The colorimetric control device 2 saves the spectral reflectances of all the measured patches in a RAM 9. After the end of saving the spectral reflectances of all the measured patches, the CPU 8 transmits a colorimetry end status to the printing apparatus 3 via the signal line 4. The printing apparatus 3 transmits a colorimetric result acquisition instruction to the colorimetric control device 2. The colorimetric control device 2 transmits the spectral reflectance data saved in the RAM 9 to the printing apparatus 3 via the signal line 4.

To change the measurement light source condition and newly execute colorimetry, the printing apparatus 3 transmits a colorimetry execution instruction to the colorimetric control device 2 by using measurement light source conditions for new measurement as arguments. Upon completion of colorimetry under all the measurement light source conditions, the printing apparatus 3 converts the received spectral reflectance data into chromaticities in a desired color space such as CIEXYZ or CIEL*a*b* by using the standard field of view and the standard luminosity function. When the colorimeter 1 measures a strip formed from a plurality of patch lines, the colorimetric control device 2 drives the sheet moving motor 14 to move a sheet, and performs the same colorimetric operation as that described above for each patch line.

Figure 6:
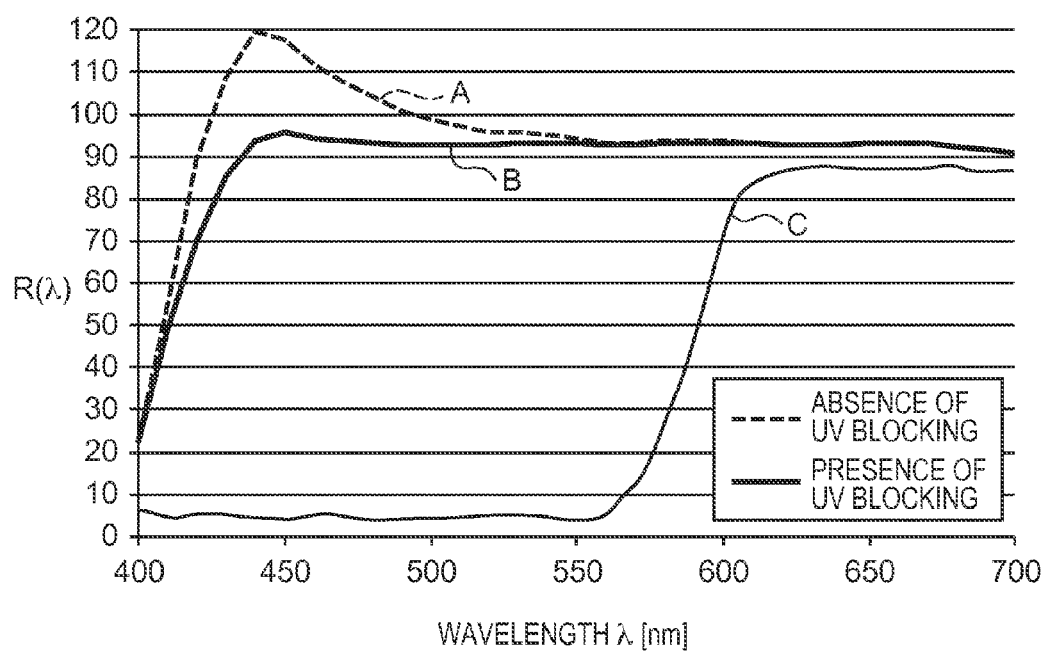
FIG. 6 is a graph showing the spectral reflectance of a fluorescent brightener-added sheet.

In the embodiment, a table which associates each sheet type and a cutoff start wavelength λcutoff is saved in advance a ROM 18 in FIG. 1. The cutoff start wavelength λcutoff is set in advance based on the result of measuring spectral reflectances of a sheet by the colorimeter 1 at two different intensity settings of the ultraviolet light source. For example, the spectral reflectance of a sheet is measured under two conditions, that is, a measurement light source condition (the absence of UV blocking) in which the ultraviolet light source emits light at a predetermined intensity (example of the second emission intensity) in addition to the visible light source, and a measurement light source condition (the presence of UV blocking) in which the ultraviolet light source is turned off (example of the first emission intensity) and measurement is performed using only the visible light source. Measurement results are compared in every 10 nm from 400 to 700 nm, and a shortest wavelength in a wavelength band where the difference becomes equal to or smaller than a given threshold is specified as the cutoff start wavelength λcutoff. The threshold is, for example, 0.5% on reflectance basis. Graphs A and B in FIG. 6 represent spectral reflectances obtained when a fluorescent brightener-added sheet (corresponding to white) is measured by turning on both the ultraviolet light source and visible light source (the absence of UV blocking), and when the ultraviolet light source is turned off and the spectral reflectance is measured using only the visible light source (the presence of UV blocking). As represented by the graphs A and B in FIG. 6, a comparison between the spectral reflectances reveals that the difference between these reflectances becomes equal to or smaller than 0.5% near a wavelength of 600 nm. Thus, 600 nm is stored as the cutoff start wavelength λcutoff in the ROM 18.

In the embodiment, when transmitting a colorimetry execution instruction from the printing apparatus 3 to the colorimetric control device 2, a sheet type is designated as an argument. For example, a fluorescent brightener-added sheet is designated. Upon receiving the colorimetry instruction, a cutoff circuit 17 in FIG. 1 reads out, from the ROM 18, a cutoff start wavelength λcutoff corresponding to the sheet type designated as the argument. When the cutoff circuit 17 receives spectral reflectance data measured by the colorimeter 1, it executes cutoff in accordance with a cutoff instruction from the CPU 8. In the embodiment, cutoff means not storing on purpose a spectral reflectance serving as a measurement result from the colorimeter 1 in the RAM 9. The colorimeter 1 continuously outputs spectral reflectance data in every 10 nm from a wavelength of 400 nm to 700 nm. The cutoff circuit 17 counts the wavelength points of received data, as needed, and in execution of cutoff, stores, in the RAM 9, only spectral reflectances in a wavelength band shorter than the cutoff start wavelength λcutoff. To the contrary, spectral reflectances in a wavelength band equal to or longer than the cutoff start wavelength λcutoff are not stored in the RAM 9. This can reduce the amount of storage in the RAM 9.

Figure 2:
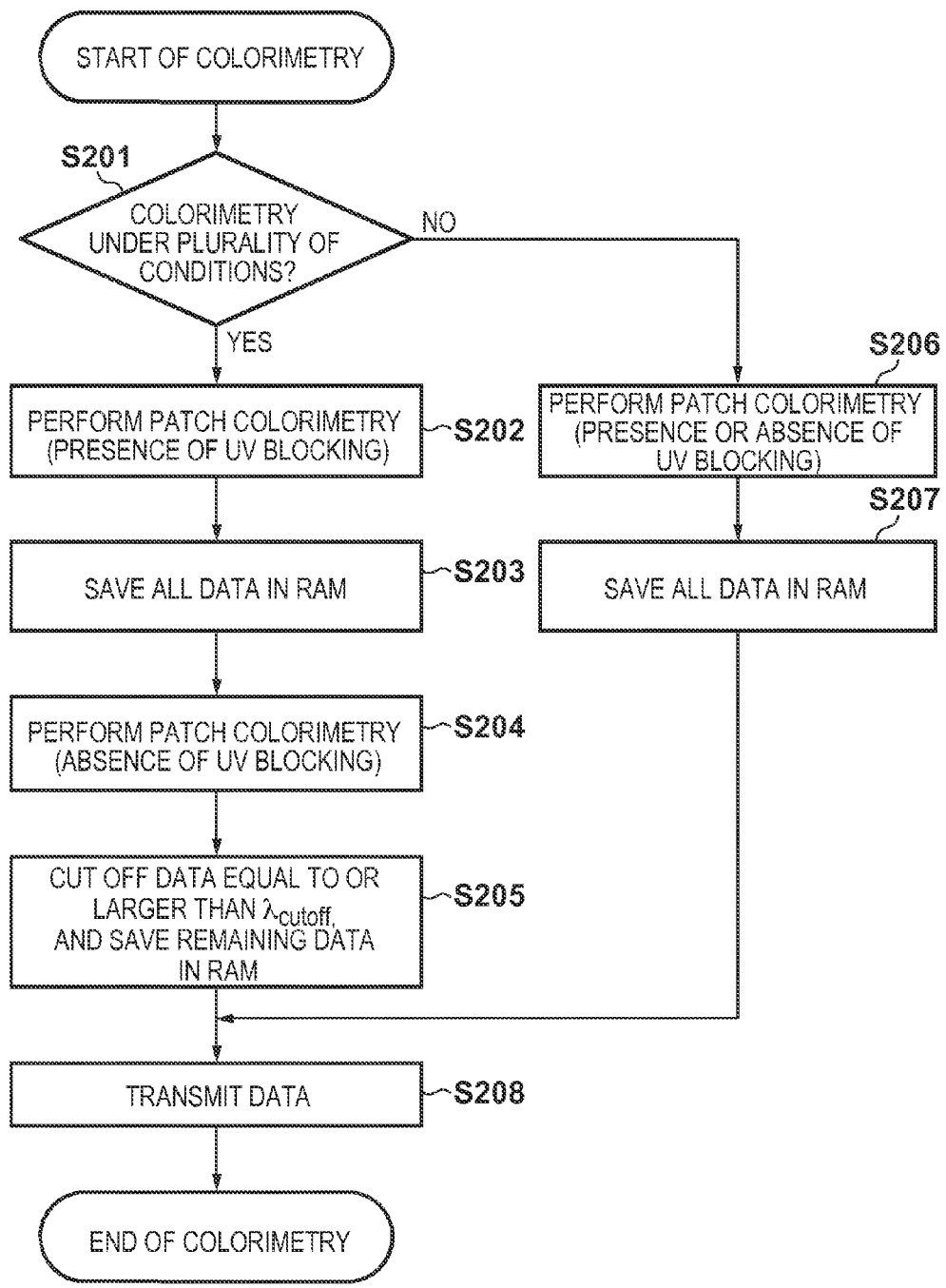
FIG. 2 is a flowchart showing the sequence of a measurement method in the first embodiment.

FIG. 2 is a flowchart showing the sequence of a measurement method in the first embodiment. When the colorimetric control device 2 receives a colorimetry execution instruction from the printing apparatus 3, it moves a sheet to the colorimetric position and starts colorimetry. After the start of colorimetry, in step S201, the CPU 8 determines, based on contents described in the colorimetry execution instruction, whether to perform colorimetry under a plurality of measurement light source conditions. In the embodiment, a case in which colorimetry is performed using visible light for one patch (the presence of UV blocking) and further performed using ultraviolet light and visible light (the absence of UV blocking) will be determined as execution of colorimetry under a plurality of measurement light source conditions. If the colorimetry execution instruction describes only either colorimetry using visible light or colorimetry using ultraviolet light and visible light, the process advances to step S206.

In step S206, the colorimetric control device 2 transmits, to the colorimeter 1, the measurement light source condition and measurement patch count designated by the printing apparatus 3, and controls the colorimeter 1 to execute colorimetry (measurement of the spectral reflectance). The colorimeter 1 controls emission from the ultraviolet light source and visible light source at predetermined emission intensities in accordance with the settings of the designated measurement light source condition. Upon the lapse of the preliminary lighting time after lighting, the colorimeter 1 transmits a colorimetry start possible status to the colorimetric control device 2. Upon receiving the colorimetry start possible status, the colorimetric control device 2 drives the colorimeter moving motor 13 and starts movement of the colorimeter 1. The colorimetric control device 2 counts the moving amount of the colorimeter 1. When a sensor mounted on the colorimeter 1 to detect light reflected by a sheet reaches a position above a desired colorimetry start position, the colorimetric control device 2 outputs a scan colorimetry execution instruction to the colorimeter 1. In accordance with the scan colorimetry execution instruction, the colorimeter 1 measures spectral reflectances by the designated patch count. After the end of measuring all spectral reflectances by the designated patch count, the colorimeter 1 (colorimetric apparatus) transmits a successful measurement status and the spectral reflectances of all the measured patches in a wavelength band of 400 to 700 nm in every 10 nm to the colorimetric control device 2. In step S207, the colorimetric control device 2 stores all the received spectral reflectance data in the RAM 9. After that, the colorimetric control device 2 drives the colorimeter moving motor 13 to return the colorimeter 1 to a position before measurement. Then, the process advances to step S208.

In step S208, the colorimetric control device 2 transmits a data transmission request to the printing apparatus 3. If the colorimetric control device 2 receives a receivable status from the printing apparatus 3, it starts transmission of the spectral reflectance data, and transmits all the spectral reflectance data stored in the RAM 9. If the colorimetric control device 2 receives a normal reception end status from the printing apparatus 3, it clears the RAM 9. If there is a patch line (strip) to be successively measured next, the printing apparatus 3 transmits a new strip colorimetry instruction to the colorimetric control device 2. If the colorimetric processing is to end, the printing apparatus 3 transmits a colorimetry end instruction to the colorimetric control device 2. If the colorimetric control device 2 receives the new strip colorimetry instruction, it drives the sheet moving motor 14 to move the next strip to the colorimetric position. If the printing apparatus 3 transmits a colorimetry end instruction to the colorimetric control device 2, it calculates a chromaticity value based on the spectral reflectance data received from the colorimetric control device 2.

If the colorimetric control device 2 determines in step S201 to perform colorimetry under a plurality of measurement light source conditions, the process advances to step S202. FIG. 2 shows an example of measuring a spectral reflectance with the A light source in the presence of UV blocking and the absence of UV blocking. In step S202, the colorimetric control device 2 first instructs the colorimeter 1 about colorimetry with the A light source in the presence of UV blocking. Similar to step S206, the colorimeter 1 turns on the visible light source at an emission intensity stored in correspondence with the setting of the measurement light source condition. Since UV blocking is set in step S202, only the visible light source is turned on without turning on the ultraviolet light source (light source control). Then, similar to step S206, preliminary lighting is performed, and the colorimeter moving motor 13 is moved to execute scan colorimetry. After the end of scan colorimetry, the colorimetric control device 2 stores all the received spectral reflectance data in the RAM 9 in step S203, similar to step S207. The colorimeter moving motor 13 is driven to return the colorimeter 1 to the position before measurement, and the process advances to step S204.

In step S204, the colorimetric control device 2 transmits, to the colorimeter 1, a measurement light source condition different from one executed in step S202 out of the measurement light source conditions designated by the printing apparatus 3. At the same time, the colorimetric control device 2 reads out, from the ROM 18, a cutoff start wavelength corresponding to the sheet type designated by the printing apparatus 3, and transfers it to the cutoff circuit 17. Similar to step S202, the colorimeter 1 turns on the ultraviolet light source and visible light source at respective emission intensities corresponding to the measurement light source condition (light source control). Similar to step S206, preliminary lighting is performed, and the colorimeter moving motor 13 is moved to execute scan colorimetry. After the end of scan colorimetry, the colorimeter 1 transmits all the measured spectral reflectance data to the colorimetric control device 2, and the process advances to step S205.

In step S205, the colorimetric control device 2 receives spectral reflectance data from the colorimeter 1 via the cutoff circuit 17. Every time the cutoff circuit 17 receives one spectral reflectance data, it counts a wavelength (wavelength region, band) corresponding to the received data. If the wavelength (wavelength region, band) is shorter than a cutoff start wavelength λcutoff set before measurement, the cutoff circuit 17 stores the received data in the RAM 9. If the wavelength (wavelength region, band) corresponding to the data is longer than the cutoff start wavelength λcutoff, the cutoff circuit 17 cuts off spectral reflectance data to be received subsequently, and does not store them in the RAM 9. Although the colorimeter 1 outputs 31 spectral reflectance measurement values, the number of spectral reflectance measurement values to be stored in the RAM 9 by the cutoff circuit 17 is smaller than 31. The above processing is performed for all patches, and then the process advances to step S208. The two measurement light source conditions have been described. For three or more conditions, steps S204 and S205 are repeated by the remaining number of measurement light source conditions after the end of step S208.

At the end of the processing shown in FIG. 2, data corresponding to a wavelength band longer than the cutoff start wavelength λcutoff does not exist for spectral reflectances in the second and subsequent conditions transmitted from the colorimetric control device 2 to the printing apparatus 3. When calculating a chromaticity value based on spectral reflectance data, the printing apparatus 3 performs calculation by using spectral reflectance data in the first condition for data in a wavelength band longer than the cutoff start wavelength λcutoff in the second and subsequent conditions.

When the light source spectral intensity distribution (spectral luminance factor) in the visible light region differs between the first condition and the nth and subsequent conditions, a spectral reflectance Rn(λ) in the visible light region is calculated according to equation (1):

$$Rn(\lambda) = Pn(\lambda)/P1(\lambda) \times R1(\lambda) \quad (1)$$

where Rn(λ) is the spectral reflectance on a wavelength side longer than the cutoff start wavelength λcutoff in the nth condition, Pn(λ) is the light source spectral intensity on the wavelength side longer than the cutoff start wavelength λcutoff in the nth condition, P1(λ) is the light source spectral intensity on a wavelength side longer than the cutoff start wavelength λcutoff in the first condition, and R1(λ) is the spectral reflectance on the wavelength side longer than the cutoff start wavelength λcutoff in the first condition.

Spectral reflectance data at 31 points (bands) in every 10 nm from 400 to 700 nm were measured using a patch chart (Fogra Media Wedge 3.0 (72)) on a sheet at excited wavelengths of ultraviolet light in a wavelength band of up to 600 nm. The size of spectral reflectance data is 2 bytes per point (per wavelength/band). As a result, a color difference from a case in which the embodiment was not employed was as small as maximum ΔE0095%=0.05 or less. It was confirmed that the amount of storage in the buffer (RAM 9) and the transmission data amount were reduced by 16% or more in measurement under two conditions, and 21% or more in measurement under three conditions. In the first embodiment, when the spectral reflectance is measured under a plurality of measurement light source conditions, the buffer storage amount and data transmission amount can be efficiently reduced with a very small color difference. In FIG. 2, the measurement order of steps S202 and S203 and that of steps S204 and S205 may be reversed. Alternatively, steps S202 and S205 may be swapped in FIG. 2. More specifically, patch colorimetry in the absence of UV blocking is performed in step S202, and spectral reflectance data at 31 points are stored in the RAM 9 in step S203. Then, patch colorimetry in the presence of UV blocking is performed in step S204, and spectral reflectance data corresponding to a wavelength band shorter than the cutoff start wavelength λcutoff are stored in the RAM 9 in step S205.

Second Embodiment

In the second embodiment, a colorimetric control device 2 shown in FIG. 1 incorporates a comparison circuit 16. The comparison circuit 16 calculates, for each wavelength, the difference between spectral reflectance data of a reference patch image of the sheet color (paper white) under a given measurement light source condition and spectral reflectance data under another measurement light source condition. A shortest wavelength in a wavelength band where the difference becomes equal to or smaller than a threshold is specified as the cutoff start wavelength λcutoff.

In the second embodiment, before measurement under a plurality of measurement light source conditions as described in the first embodiment, the spectral reflectance of an unprinted portion (to be referred to as paper white (reference patch image) hereinafter) on a sheet is measured in a case (example of the first measurement control) in which only the visible light source is turned on, and a case (example of the second measurement control) in which the ultraviolet light source and visible light source are turned on. The comparison circuit 16 compares these measurement results, and a wavelength output from the comparison circuit 16 is specified as the cutoff start wavelength λcutoff.

Figure 3:
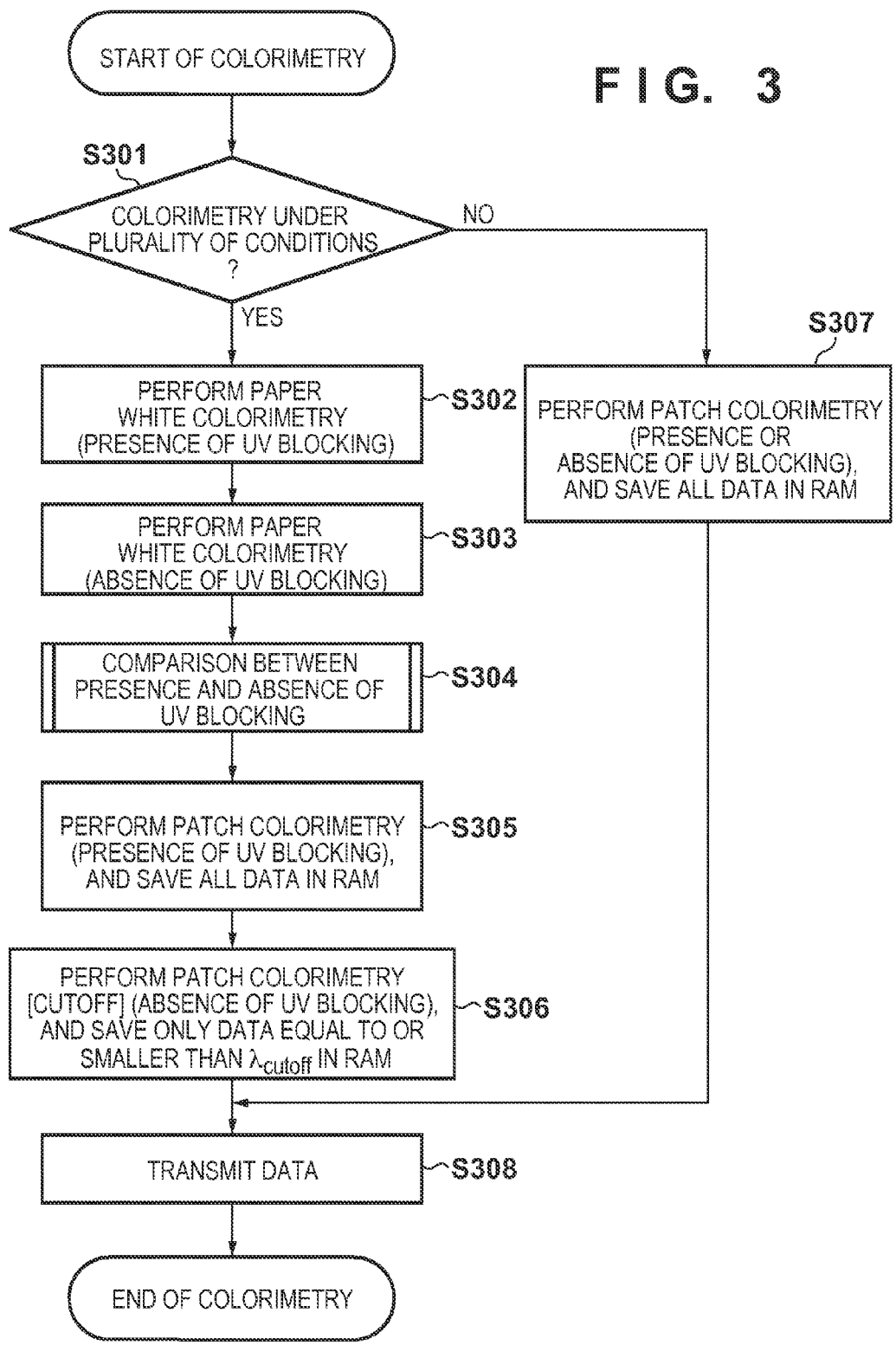
FIG. 3 is a flowchart showing the sequence of a measurement method in the second embodiment.

FIG. 3 is a flowchart showing the sequence of a measurement method in the second embodiment. When the colorimetric control device 2 receives a colorimetry execution instruction from a printing apparatus 3, it moves a sheet to the colorimetric position and starts colorimetry. In step S301, a CPU 8 determines, based on contents described in the colorimetry execution instruction, whether to perform colorimetry under a plurality of measurement light source conditions. If the CPU 8 determines to perform colorimetry under one measurement light source condition, the process advances to step S307. In step S307, the spectral reflectance is measured and saved in a RAM 9, similar to steps S206 and S207 in the first embodiment. After the processing in step S307, the process advances to step S308. Step S308 is the same as step S208 of FIG. 2.

If the CPU 8 determines in step S301 to perform colorimetry under a plurality of measurement light source conditions, the process advances to step S302. In step S302, the colorimetric control device 2 rotates a colorimeter moving motor 13 via a mechatronics control unit 10 to move a colorimeter 1 to a patch at the paper white portion of a sheet. Upon completion of the movement, the colorimetric control device 2 stops the rotation of the colorimeter moving motor 13. In step S302, the colorimetric control device 2 sets the presence of UV blocking in the measurement light source condition, and transmits a colorimetry preparation instruction to the colorimeter 1. The colorimeter 1 preliminarily turns on only the visible light source. Upon the lapse of the preliminary lighting time, the colorimeter 1 transmits a status to the colorimetric control device 2 to represent that the preliminary lighting has ended normally. Thereafter, the colorimetric control device 2 transmits a colorimetry execution instruction to the colorimeter 1. The colorimeter 1 measures the spectral reflectance of the patch at the paper white portion, and transmits the spectral reflectance measurement result to the colorimetric control device 2. The colorimetric control device 2 receives the measurement value and temporarily saves it in the comparison circuit 16, and the process advances to step S303.

In step S303, the colorimetric control device 2 sets the absence of UV blocking in the measurement light source condition, and transmits a colorimetry preparation instruction to the colorimeter 1. Similar to step S302, the colorimeter 1 measures the spectral reflectance of the patch at the paper white portion, and transmits the spectral reflectance measurement result to the colorimetric control device 2. The colorimetric control device 2 receives the measurement value and temporarily saves it in the comparison circuit 16, and the process advances to step S304. In step S304, the comparison circuit 16 compares the spectral reflectance data saved in step S302 with the spectral reflectance data saved in step S303.

Figure 4:
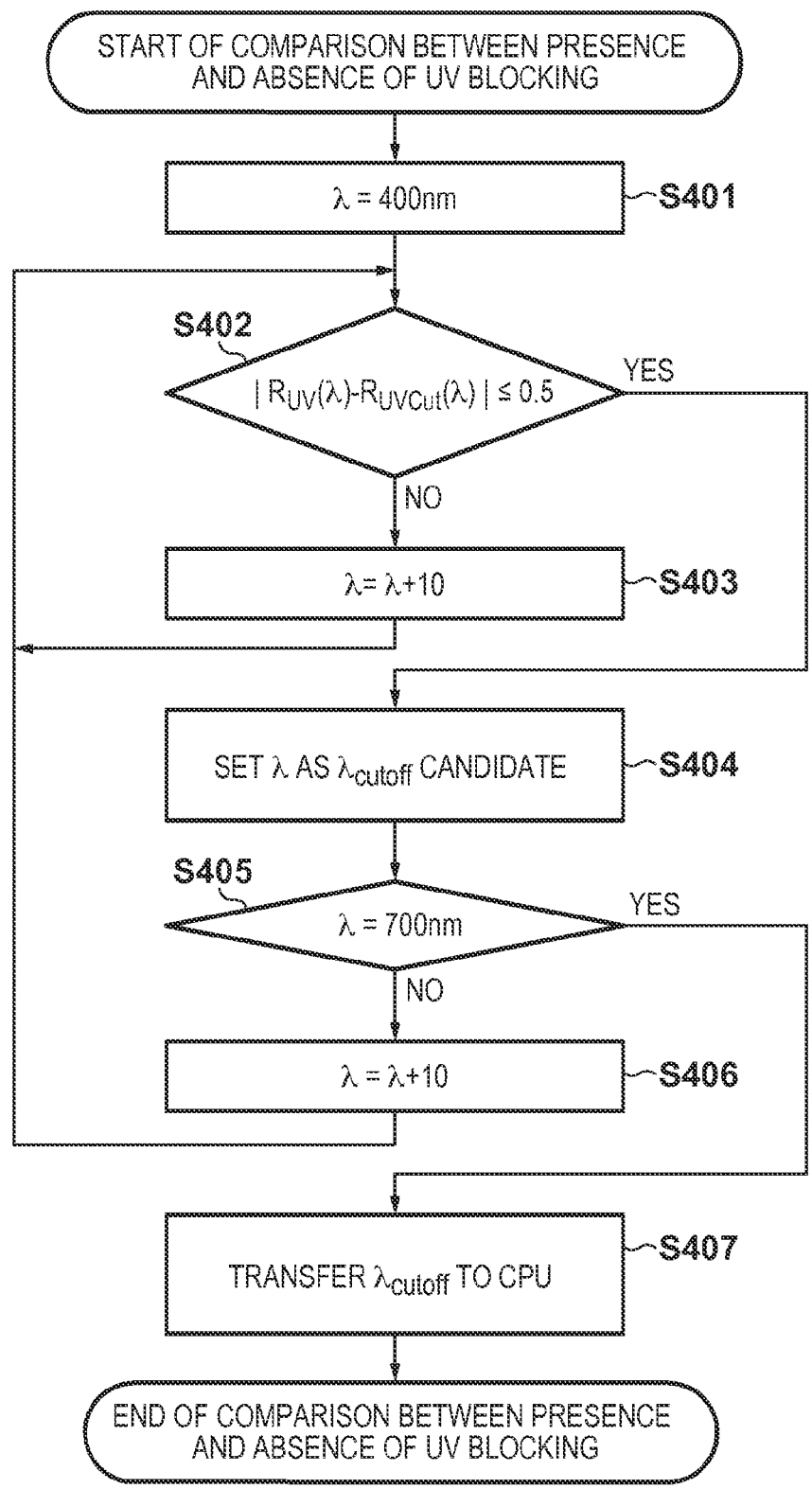
FIG. 4 is a flowchart showing the sequence of processing in step S304.

FIG. 4 is a flowchart showing the sequence of the processing in step S304. In step S401, the comparison circuit 16 sets a comparison start wavelength $\lambda$ to 400 nm, and the process advances to step S402. In step S402, the comparison circuit 16 calculates the absolute value of the difference between a spectral reflectance RUVcut($\lambda$) saved in step S302 and a spectral reflectance RUV($\lambda$) saved in step S303, and determines whether the value is equal to or smaller than 0.5. If the comparison circuit 16 determines that the value is equal to or smaller than 0.5, the process advances to step S404. In step S404, the comparison circuit 16 stores the current wavelength (for example, 400 nm) as a candidate of the cutoff start wavelength $\lambda$cutoff. If the comparison circuit 16 determines in step S402 that the value is larger than 0.5, the current wavelength is incremented by 10 nm, and the processing in step S402 is repeated. After repeating the processing in step S402, if the comparison circuit 16 determines again in step S402 that the value is equal to or smaller than 0.5, it stores the current wavelength (for example, 410 nm) as another candidate of the cutoff start wavelength $\lambda$cutoff in step S404.

In step S405, the comparison circuit 16 determines whether the current wavelength is 700 nm. If the comparison circuit 16 determines that the current wavelength is 700 nm, the process advances to step S407, and the comparison circuit 16 transfers, as the cutoff start wavelength $\lambda$cutoff to the CPU 8, a shortest wavelength among the stored candidates of the cutoff start wavelength $\lambda$cutoff. If the comparison circuit 16 determines in step S405 that the current wavelength is not 700 nm, the current wavelength is incremented by 10 nm, and the process is repeated from step S402.

After the processing in step S407, the process advances to step S305 of FIG. 3 to start measurement of the spectral reflectance of a patch under the first measurement light source condition (the presence of UV blocking). In step S305, similar to steps S202 and S203 of FIG. 2, the spectral reflectance of the patch is measured, and all the spectral reflectance data are saved in the RAM 9. After the end of save in the RAM 9, the process advances to step S306 to measure a spectral reflectance under the second measurement light source condition (the absence of UV blocking). In step S306, similar to steps S204 and S205 of FIG. 2, the spectral reflectance is measured, and the spectral reflectance data is saved in the RAM 9 while executing cutoff based on the cutoff start wavelength $\lambda$cutoff transferred to the CPU 8 in step S304.

The second embodiment has described the two measurement light source conditions. For three or more measurement light source conditions, the processing in step S306 is repeated by the number of conditions. Upon completion of measuring spectral reflectances under all the measurement light source conditions, the process advances to step S308. In step S308, the colorimetric control device 2 transmits the spectral reflectance data for all the measurement light source conditions to the printing apparatus 3. Upon completion of transmitting the spectral reflectance data, the colorimetric control device 2 clears the RAM 9. Similar to the first embodiment, when the light source spectral intensity distribution in the visible light region differs between the first condition and the nth and subsequent conditions, the printing apparatus 3 calculates Rn($\lambda$) according to equation (1), and calculates chromaticity values in the second and subsequent conditions by using the Rn($\lambda$) value.

In the second embodiment, the comparison circuit 16 measures the influence of a fluorescent brightener for each sheet to be measured, obtains a cutoff start wavelength $\lambda$cutoff suited to each sheet, and then measures a spectral reflectance. Even when a new sheet is added or the user is to use an unregistered sheet, the cutoff start wavelength $\lambda$cutoff can be automatically obtained. Similar to the first embodiment, when the spectral reflectance is measured under a plurality of measurement light source conditions, the buffer storage amount and data transmission amount can be efficiently reduced with a very small color difference.

Third Embodiment

In the third embodiment, a comparison circuit 16 compares the magnitude of a spectral reflectance under the first or second measurement light source condition with a predetermined reflectance threshold, in addition to the comparison between a spectral reflectance under the first measurement light source condition and a spectral reflectance under the second measurement light source condition.

The absorptance by ink is high for light irradiating a high-density patch of red, yellow, or the like among patches printed on a sheet. Ultraviolet light is excited in the sheet, the reflected light becomes very weak, and the influence of the apparent fluorescent brightener decreases. That is, the difference of appearance depending on the light source decreases. Considering this, in the third embodiment, in addition to the first and second embodiments, a spectral reflectance corresponding to a wavelength determined to be free from the influence of the fluorescent brightener in appearance is also cut off. This can further reduce the buffer storage amount and data transfer amount.

FIG. 5A is a flowchart showing the sequence of processing in step S306 to be executed as the third embodiment. For measurement of spectral reflectances under the second and subsequent conditions, a colorimetric control device 2 transmits a colorimetry instruction to a colorimeter 1. After the end of measurement by the colorimeter 1, the colorimeter 1 transmits the measurement value to the colorimetric control device 2. Then, the comparison circuit 16 starts comparison for a spectral reflectance corresponding to each wavelength. First, the comparison circuit 16 sets the cutoff start wavelength $\lambda$cutoff to 400 nm, and the process advances to step S501. In step S501, the comparison circuit 16 reads out a reflectance threshold Rthreshold saved in a ROM 18. Rthreshold is a threshold for the spectral reflectance and is, for example, R($\lambda$)=9 shown in FIG. 6. In the third embodiment, if the measured spectral reflectance is lower than Rthreshold, it is determined that even a wavelength equal to or shorter than the cutoff start wavelength $\lambda$cutoff influenced by the fluorescent brightener is free from the influence of the fluorescent brightener.

In step S502, the colorimetric control device 2 receives the 400-nm spectral reflectance from the colorimeter 1, and the process advances to step S503. In step S503, the comparison circuit 16 compares the reflectance threshold Rthreshold read out from the ROM 18 with the spectral reflectance value of 400 nm received from the colorimeter 1. If the received spectral reflectance is equal to or lower than the reflectance threshold, the process advances to step S506 to cut off spectral reflectance data corresponding to the wavelength. If the received spectral reflectance is higher than the reflectance threshold, the process advances to step S504.

For example, when the patch is red, its reflectance changes with respect to the wavelength regardless of the light source, as represented by a graph C in FIG. 6. That is, not only the reflectances of wavelengths longer than the cutoff start wavelength λcutoff, but also those of wavelengths near 400 to 550 nm are cut off, and only the reflectances of wavelengths near 550 to 600 nm are stored in a RAM 9. This can greatly reduce the buffer storage amount and data transfer amount.

In step S504, the comparison circuit 16 determines whether the current wavelength falls in a wavelength band longer than the cutoff start wavelength λcutoff. If the comparison circuit 16 determines that the current wavelength falls in a wavelength band longer than the cutoff start wavelength λcutoff, the process advances to step S506 to cut off spectral reflectance data corresponding to the wavelength. If the comparison circuit 16 determines that the current wavelength falls outside a wavelength band longer than the cutoff start wavelength λcutoff, the process advances to step S505 to save spectral reflectance data corresponding to the wavelength in the RAM 9, and then to step S507. This processing is the same as that in the first and second embodiments.

In step S507, the colorimetric control device 2 determines whether the current wavelength is 700 nm. If the colorimetric control device 2 determines that the current wavelength is 700 nm, the process advances to step S308 of FIG. 3. If the colorimetric control device 2 determines that the current wavelength is not 700 nm, the process advances to step S508 to increment the wavelength by 10 nm, and then is repeated from step S502. In the third embodiment, when spectral reflectance data in the second condition is transmitted to a printing apparatus 3, the reflectance threshold Rthreshold is also transmitted together with the data in step S308 of FIG. 3.

In step S308, the printing apparatus 3 temporarily saves, in its internal RAM, the spectral reflectance data and reflectance threshold Rthreshold received from the colorimetric control device 2, and then calculates the chromaticity.

FIG. 5B is a flowchart showing the sequence of a spectral reflectance restoring method when calculating chromaticities under the second and subsequent conditions. In FIG. 5B, R1(λ) is the spectral reflectance in the first condition (the presence of UV blocking), and Rn(λ) is the spectral reflectance in the nth condition (the absence of UV blocking).

After setting 400 nm as a readout start wavelength λ, the printing apparatus 3 reads out the reflectance threshold Rthreshold in step S601, and the process advances to step S602. In step S602, the printing apparatus 3 reads out the spectral reflectance R1(λ) corresponding to 400 nm in the first condition, and the process advances to step S603. In step S603, the printing apparatus 3 determines whether the spectral reflectance R1(λ) is higher than the reflectance threshold Rthreshold.

If the printing apparatus 3 determines that the spectral reflectance R1(λ) is equal to or lower than the reflectance threshold Rthreshold, the process advances to step S606 to set R1(λ) as the spectral reflectance Rn(λ) in the nth condition, and to step S607. If the printing apparatus 3 determines that the spectral reflectance R1(λ) is higher than the reflectance threshold Rthreshold, the process advances to step S604. In step S604, the printing apparatus 3 determines whether the current wavelength λ (400 nm) is equal to or shorter than the cutoff start wavelength λcutoff. If the printing apparatus 3 determines that the current wavelength λ is longer than the cutoff start wavelength λcutoff, the process advances to step S606. Since the wavelength falls in a wavelength band longer than the cutoff start wavelength λcutoff, the spectral reflectance R1(λ) in the first condition is restored as Rn(λ). If the printing apparatus 3 determines in step S604 that the current wavelength λ is equal to or shorter than the cutoff start wavelength λcutoff, it reads out a spectral reflectance in the nth condition from the RAM of the printing apparatus 3, and restores it. After reading out the spectral reflectance, the printing apparatus 3 increments, by "1", the readout address of the spectral reflectance in the nth condition from the RAM in step S605, and the process advances to step S607.

In step S607, the printing apparatus 3 determines whether the current wavelength is 700 nm. If the printing apparatus 3 determines that the current wavelength is 700 nm, the process ends. If the printing apparatus 3 determines that the current wavelength is not 700 nm, it increments the wavelength by 10 nm in step S608, and the process is repeated from step S602. That is, if it is determined in step S607 that the current wavelength is 700 nm, this means that spectral reflectances in the nth condition have been restored for all wavelengths. The printing apparatus 3 calculates a chromaticity value in an arbitrary color space by using the restored spectral reflectance data.

As described above, the third embodiment can greatly reduce the buffer amount by setting a reflectance threshold. The third embodiment assumes that the appearance of a high-density patch of red or the like does not change regardless of the type of light source. Assuming that the spectral reflectance in the first condition is one indicated by the graph C in FIG. 6, the result of restoring the spectral reflectance in the nth condition needs to be the same as the graph C. To improve the restoration accuracy, it is preferable that the reflectance threshold Rthreshold is sufficiently close to the spectral reflectance in the first condition, such as R(λ)=9. Also, the reflectance threshold may be set in advance for each patch color and held in the printing apparatus 3.

In the third embodiment, measurement was performed under the same measurement light source condition as that in the first embodiment. When Rthreshold=9.0 and λcutoff=600 nm, a color difference from a case in which the embodiment was not employed was as small as maximum ΔE0095%=2.0 or less. It was confirmed that the buffer storage amount and transmission data amount could be reduced by about 51% in overall two-condition measurement. When Rthreshold=3.0 and λcutoff=600 nm, the color difference was as much small as maximum ΔE0095%=1.5 or less. It was confirmed that the buffer storage amount and transmission data amount could be reduced by about 42% in overall two-condition measurement. The third embodiment has described a verification result on a sheet on which a wavelength excited by ultraviolet light is 600 nm in a wide band. However, a more significant data amount reduction effect can be expected on a sheet on which excitation by ultraviolet light is small, and a sheet on which the band of an excited wavelength is narrow.

Next, the arrangement of the inkjet printing apparatus as an example of the printing apparatus in the embodiment will be explained. It is also possible to enable colorimetry and perform the processes in the first to third embodiments by combining the measurement apparatus described in the embodiment with the inkjet printing apparatus to be described below.

[Description of Inkjet Printing Apparatus]

Figure 7:
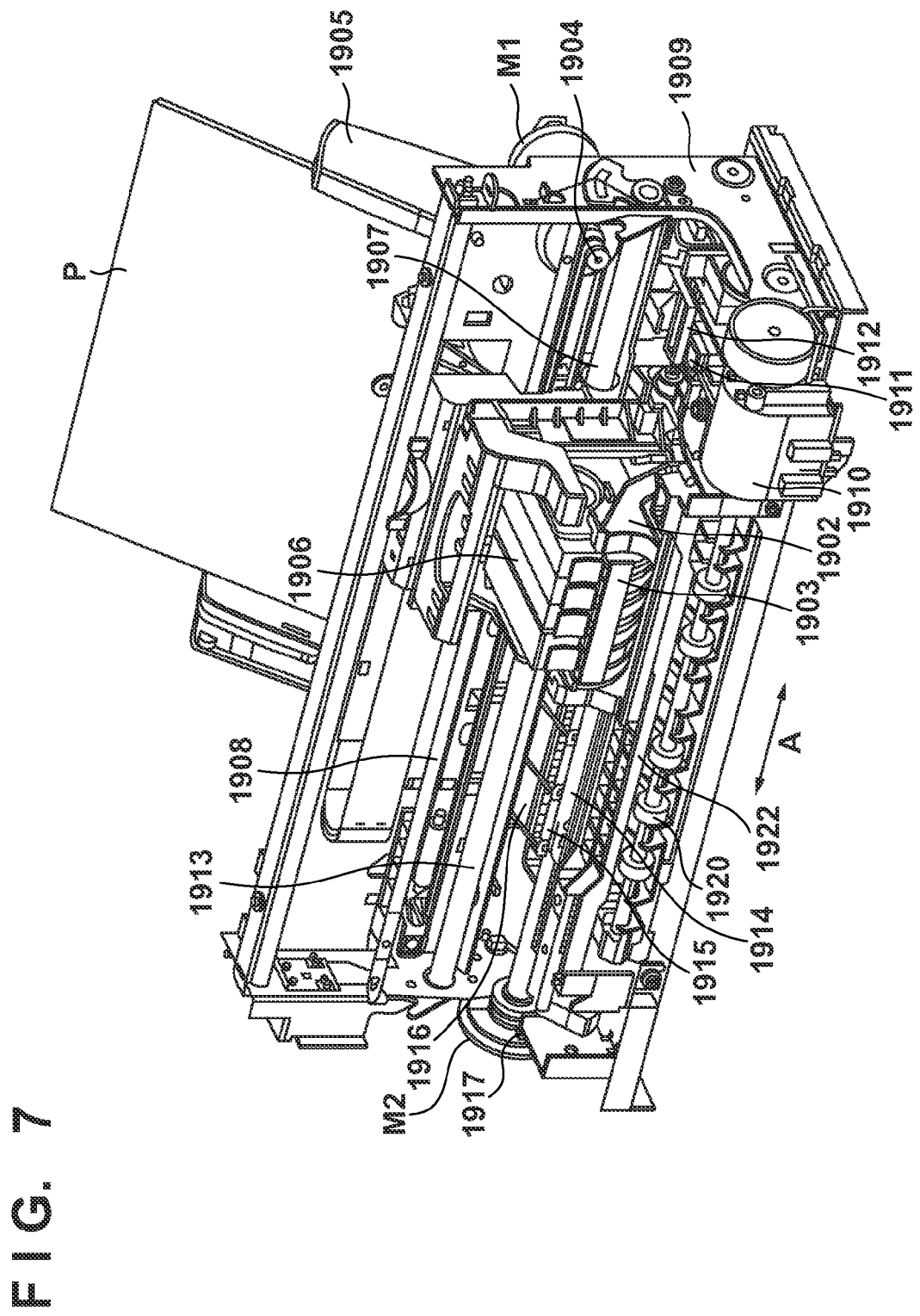
FIG. 7 is a view showing the arrangement of an inkjet printing apparatus.

FIG. 7 is an outer perspective view showing the schematic arrangement of the inkjet printing apparatus as a typical embodiment of the present invention.

The inkjet printing apparatus shown in FIG. 7 prints as follows. A transmission mechanism 1904 transmits a driving force generated by a carriage motor M1 to a carriage 1902 which supports a printhead 1903 for printing by discharging ink according to an inkjet method, thereby reciprocating the carriage 1902 in directions indicated by an arrow A. At the same time, a sheet P such as printing paper is fed via a paper feed mechanism 1905, and conveyed to a printing position. At the printing position, the printhead 1903 discharges ink onto the sheet P.

To maintain a good state of the printhead 1903, the carriage 1902 is moved to the position of a recovery device 1910 to intermittently execute discharge recovery processing for the printhead 1903.

In addition to the printhead 1903, an ink cartridge 1906 which stores ink to be supplied to the printhead 1903 is mounted on the carriage 1902 of the inkjet printing apparatus. The ink cartridge 1906 is detachable from the carriage 1902.

The inkjet printing apparatus shown in FIG. 7 can print in color. For this purpose, four ink cartridges which store magenta (M), cyan (C), yellow (Y), and black (K) inks, respectively, are mounted on the carriage 1902. These four ink cartridges are independently detachable.

The carriage 1902 and printhead 1903 can achieve and maintain necessary electrical connection by properly bringing their joint surfaces into contact with each other. By applying energy in accordance with a print signal, the printhead 1903 prints by selectively discharging ink from a plurality of orifices. Especially, the printhead 1903 in the embodiment employs an inkjet method of discharging ink using thermal energy. The printhead 1903 includes electrothermal transducers for generating thermal energy. Electrical energy applied to the electrothermal transducers is converted into thermal energy. Ink is discharged from orifices by using a pressure change caused by growth and contraction of bubbles generated by film boiling upon applying the thermal energy to ink. The electrothermal transducers are arranged in correspondence with respective orifices. By applying a pulse voltage to a corresponding electrothermal transducer in accordance with a print signal, ink is discharged from a corresponding orifice. Note that the inkjet method is not limited to this, and is arbitrarily a method using a piezoelectric element, one using a MEMS element, or one using an electrostatic element.

As shown in FIG. 7, the carriage 1902 is coupled to part of a driving belt 1907 of the transmission mechanism 1904 which transmits the driving force of the carriage motor M1. The carriage 1902 is guided and supported slidably along a guide shaft 1913 in the directions indicated by the arrow A. The carriage 1902 reciprocates along the guide shaft 1913 by forward rotation and reverse rotation of the carriage motor M1. A scale 1908 (CR encoder film) is arranged in the moving direction (directions indicated by the arrow A) of the carriage 1902 to indicate the absolute position of the carriage 1902. In the embodiment, the scale 1908 is formed by printing black bars at necessary pitches on a transparent PET film. One end of the scale 1908 is fixed to a chassis 1909, and the other end is supported by a leaf spring (not shown).

In the inkjet printing apparatus, a platen (not shown) is arranged to face the orifice surface of the printhead 1903 on which orifices (not shown) are formed. Simultaneously when the carriage 1902 supporting the printhead 1903 is reciprocated by the driving force of the carriage motor M1, a print signal is supplied to the printhead 1903 to discharge ink, thereby printing at the full width on the sheet P conveyed onto the platen.

A conveyance motor M2 drives a conveyance roller 1914 in FIG. 7 to convey the sheet P. A pinch roller 1915 makes the sheet P abut against the conveyance roller 1914 by a spring (not shown). A pinch roller holder 1916 rotatably supports the pinch roller 1915. A conveyance roller gear 1917 is fixed to one end of the conveyance roller 1914. The conveyance roller 1914 is driven by rotation of the conveyance motor M2 that is transmitted to the conveyance roller gear 1917 via an intermediate gear (not shown).

A discharge roller 1920 discharges, from the inkjet printing apparatus, the sheet P bearing an image formed by the printhead 1903. The discharge roller 1920 is driven by transmitting rotation of the conveyance motor M2. The discharge roller 1920 abuts against a spur roller (not shown) which press-contacts the sheet P by a spring (not shown). A spur holder 1922 rotatably supports the spur roller.

In the inkjet printing apparatus, as shown in FIG. 7, the recovery device 1910 for recovering the printhead 1903 from a discharge failure is arranged at a desired position (for example, a position corresponding to the home position) outside the range (outside the printing region) of reciprocating motion for the printing operation of the carriage 1902 on which the printhead 1903 is mounted.

The recovery device 1910 includes a capping mechanism 1911 which caps the orifice surface of the printhead 1903, and a wiping mechanism 1912 which cleans the orifice surface of the printhead 1903. The recovery device 1910 performs discharge recovery processing. More specifically, ink is forcibly discharged from orifices by a suction arrangement (for example, a suction pump) in the recovery device in synchronism with capping of the orifice surface by the capping mechanism 1911. This removes viscosity-increased ink, bubbles, and the like in the ink channel of the printhead 1903.

In a non-printing operation or the like, the capping mechanism 1911 caps the orifice surface of the printhead 1903 so that the printhead 1903 can be protected, and evaporation and drying of ink can be prevented. The wiping mechanism 1912 is arranged near the capping mechanism 1911, and wipes ink droplets attached to the orifice surface of the printhead 1903.

The capping mechanism 1911 and wiping mechanism 1912 can normally maintain the ink discharge state of the printhead 1903.

[Control Arrangement of Inkjet Printing Apparatus]

FIG. 8 is a block diagram showing the control arrangement of the inkjet printing apparatus shown in FIG. 7.

As shown in FIG. 8, a control unit 2000 includes an MPU 2001, ROM 2002, application specific integrated circuit (ASIC) 2003, RAM 2004, system bus 2005, and A/D converter 2006. The ROM 2002 stores programs corresponding to control sequences (to be described later), necessary tables, and other permanent data. The ASIC 2003 generates control signals to control the carriage motor M1, conveyance motor M2, and printhead 1903. The RAM 2004 provides an image data rasterization area, a work area for executing a program, and the like. The system bus 2005 connects the respective blocks to each other to exchange data. The A/D converter 2006 receives an analog signal from a sensor group (to be described later), A/D-converts it, and supplies the digital signal to the MPU 2001.

Referring to FIG. 8, a host apparatus 2010 is a computer (or a reader for reading an image, a digital camera, or the like) serving as an image data supply source. The host apparatus 2010 and inkjet printing apparatus transmit/receive image data, commands, status signals, and the like to/from each other via an interface (I/F) 2011.

A switch group 2020 includes switches for accepting instruction inputs by the operator, such as a power switch 2021, a print switch 2022 for instructing the start of printing, and a recovery switch 2023 for designating activation of processing (recovery processing) for maintaining good ink discharge performance of the printhead 1903. A sensor group 2030 includes sensors for detecting the state of the inkjet printing apparatus, such as a position sensor 2031 (for example, a photocoupler) for detecting the home position, and a temperature sensor 2032 arranged at an appropriate portion in the inkjet printing apparatus to detect the ambient temperature.

A carriage motor driver 2040 drives the carriage motor M1 to reciprocally scan the carriage 1902 in the directions indicated by the arrow A shown in FIG. 7. A conveyance motor driver 2042 drives the conveyance motor M2 to convey the sheet P.

At the time of print scanning by the printhead 1903, the ASIC 2003 transfers printing element (discharge heater) driving data to the printhead while directly accessing the storage area of the ROM 2002.

Note that the ink cartridge 1906 and printhead 1903 are separable in the arrangement shown in FIG. 7, but may be integrated to configure an interchangeable head cartridge.

A droplet to be discharged from the printhead is ink, and a liquid contained in the ink tank is ink. However, the content is not limited to ink. For example, the ink tank may contain a processing liquid to be discharged to a sheet in order to improve the fixation and water resistance of a printed image and improve the image quality.

The inkjet printing apparatus adopts an arrangement (for example, an electrothermal transducer and laser beam) which generates thermal energy as energy used to discharge ink. By using the method of changing the ink state by thermal energy, the printing density and resolution can be increased.

The inkjet printing apparatus may employ a full-line type printhead having a length corresponding to the maximum width of a sheet, which is configured by combining a plurality of printheads to satisfy the length, or as one integrated printhead.

The printhead is not limited to a cartridge type printhead integrated with an ink tank, and may be an interchangeable chip type printhead which is mounted on the apparatus main body and can be electrically connected to the apparatus main body and receive ink from it.

The inkjet printing apparatus in the embodiment may take the form of an inkjet printing apparatus integrally or separately arranged as the image output terminal of an information processing apparatus such as a computer, the form of a copying apparatus combined with a reading apparatus, or the form of a facsimile apparatus having transmission and reception functions.

As described in the first to third embodiments, when measuring spectral reflectances by using a plurality of light source conditions, the state of excitation by ultraviolet light on a sheet is measured in advance, and spectral reflectance data in a wavelength band free from the influence of excitation by ultraviolet light are commonly set. As a result, when measuring spectral reflectances under a plurality of light source conditions, the buffer storage amount and data transfer amount can be reduced with a small color difference.

In the first to third embodiments, from the viewpoint of closed calibration and seamless colorimetry after printing, the colorimetric control device 2 is controlled by the printing apparatus 3. However, the colorimetric control device 2 may be controlled by a general-purpose PC or the like. The first to third embodiments have exemplified one ultraviolet light source and one visible light source. To make a light source condition close to that of a reference light source more strictly, a plurality of ultraviolet light sources having different emission wavelengths may be arranged to optimize the emission intensities of the respective ultraviolet light sources in accordance with respective light source conditions.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-072339, filed Mar. 27, 2012, which is hereby incorporated by reference herein in its entirety.

What is claimed is:

1. A colorimetric apparatus comprising:
an irradiation unit configured to be able to irradiate a sheet with at least one of visible light and ultraviolet light;
an acquisition unit configured to acquire a spectral reflectance for each of a plurality of wavelength regions based on light reflected by the sheet;
a memory unit; and
a storing unit configured to store, in said memory unit, a spectral reflectance acquired by said acquisition unit in a case where the sheet is irradiated with the visible light, wherein said storing unit stores, in said memory unit, a spectral reflectance in a wavelength region shorter than a predetermined wavelength among spectral reflectances acquired by said acquisition unit in a case where the sheet is irradiated with both the visible light and the ultraviolet light.

2. The apparatus according to claim 1, further comprising a transfer unit configured to transfer a spectral reflectance acquired by said acquisition unit to said storing unit.

3. The apparatus according to claim 1, wherein said storing unit further stores, in said memory unit, a spectral reflectance higher than a spectral reflectance threshold among the spectral reflectances acquired by said acquisition unit in a case where the sheet is irradiated with both the visible light and the ultraviolet light.

4. The apparatus according to claim 1, wherein the predetermined wavelength is determined based on a spectral reflectance acquired in a case where the sheet is irradiated with the visible light, and a spectral reflectance acquired in a case where the sheet is irradiated with both the visible light and the ultraviolet light.

5. The apparatus according to claim 1, wherein said acquisition unit acquires a spectral reflectance based on light reflected by a single image printed on the sheet.

6. A printing apparatus comprising:
a colorimetric apparatus defined in claim 1; and
a printing unit which prints an image on a sheet.

7. A colorimetric apparatus comprising:
an irradiation unit configured to be able to irradiate a sheet with at least one of visible light and ultraviolet light;
an acquisition unit configured to acquire a spectral reflectance for each of a plurality of wavelength regions based on light reflected by the sheet;
a memory unit; and
a storing unit configured to store, in said memory unit, a spectral reflectance acquired by said acquisition unit in a case where the sheet is irradiated with both the visible light and the ultraviolet light, and store, in said memory unit, a spectral reflectance in a wavelength region shorter than a predetermined wavelength among spectral reflectances acquired by said acquisition unit in a case where the sheet is irradiated with the visible light.

8. A colorimetric method comprising:
a first acquisition step of acquiring a spectral reflectance for each of a plurality of predetermined wavelength regions based on light reflected by a sheet in a case where the sheet is irradiated with visible light;
a first storing step of storing, in a memory unit, a spectral reflectance acquired in the first acquisition step;
a second acquisition step of acquiring a spectral reflectance for each of the plurality of wavelength regions based on light reflected by the sheet in a case where the sheet is irradiated with both visible light and ultraviolet light; and
a second storing step of storing, in the memory unit, a spectral reflectance in a wavelength region shorter than a predetermined wavelength among spectral reflectances acquired in the second acquisition step.

9. A colorimetric method comprising:
a first acquisition step of acquiring a spectral reflectance for each of a plurality of predetermined wavelength regions based on light reflected by a sheet in a case where the sheet is irradiated with both visible light and ultraviolet light;
a first storing step of storing, in a memory unit, a spectral reflectance acquired in the first acquisition step;
a second acquisition step of acquiring a spectral reflectance for each of the plurality of wavelength regions based on light reflected by the sheet in a case where the sheet is irradiated with visible light; and
a second storing step of storing, in the memory unit, a spectral reflectance in a wavelength region shorter than a predetermined wavelength among spectral reflectances acquired in the second acquisition step.

* * * * *